United States Patent [19]
Buelna et al.

[11] Patent Number: 5,836,956
[45] Date of Patent: Nov. 17, 1998

[54] WOUND CLOSURE APPARATUS AND METHOD

[75] Inventors: Terrence J. Buelna, Laguna Beach; Wayne A. Noda, Mission Viejo; Paul Lubock, Laguna Niguel, all of Calif.

[73] Assignee: C.R. Bard, Inc., Murray Hill, N.J.

[21] Appl. No.: 891,957

[22] Filed: Jul. 14, 1997

Related U.S. Application Data

[63] Continuation of Ser. No. 502,482, Jul. 14, 1995, Pat. No. 5,700,273.

[51] Int. Cl.$^6$ ........................................ A61B 17/04
[52] U.S. Cl. ............................... 606/148; 606/144
[58] Field of Search ...................... 606/148, 144, 606/143, 145, 139, 233, 185; 128/898

[56] References Cited

U.S. PATENT DOCUMENTS

| | | |
|---|---|---|
| 3,716,058 | 2/1973 | Tanner, Jr., James . |
| 4,493,323 | 1/1985 | Albright et al. . |
| 4,669,473 | 6/1987 | Richards et al. . |
| 4,744,364 | 5/1988 | Kensey, Kenneth . |
| 4,935,027 | 6/1990 | Yoon . |
| 5,021,059 | 6/1991 | Kensey et al. . |
| 5,053,046 | 10/1991 | Janese, Woodrow . |
| 5,061,274 | 10/1991 | Kensey, Kenneth . |
| 5,085,661 | 2/1992 | Moss, Gerald . |
| 5,141,515 | 8/1992 | Eberbach . |
| 5,171,259 | 12/1992 | Inoue, Kanji . |
| 5,176,692 | 1/1993 | Wilk et al. . |
| 5,222,508 | 6/1993 | Contarini, Osvaldo . |
| 5,257,637 | 11/1993 | El Gazayerli, Mohamed . |
| 5,281,234 | 1/1994 | Wilk et al. . |
| 5,282,827 | 2/1994 | Kensey et al. . |
| 5,304,184 | 4/1994 | Hathaway et al. . |
| 5,320,632 | 6/1994 | Heidmueller, Elke . |
| 5,356,432 | 10/1994 | Rutkow et al. . |
| 5,364,408 | 11/1994 | Gordon . |
| 5,368,601 | 11/1994 | Sauer et al. . |
| 5,374,275 | 12/1994 | Bradley et al. . |
| 5,383,477 | 1/1995 | DeMatteis . |
| 5,391,182 | 2/1995 | Chin, Albert . |
| 5,391,183 | 2/1995 | Janaen et al. . |
| 5,397,331 | 3/1995 | Himpens et al. . |
| 5,403,329 | 4/1995 | Hinchliffe . |

(List continued on next page.)

FOREIGN PATENT DOCUMENTS

| | | |
|---|---|---|
| WO 95/13021 | 5/1995 | WIPO . |
| Wo 96/29012 | 9/1996 | WIPO . |

OTHER PUBLICATIONS

"Collagen Application for Sealing of Arterial Puncture Sites in Comparison to Pressure Dressing: A Randomized Trial", Catherterization and Cardiovascular Diagnosis 27:298–302 (1992).

"Selection of Guiding Catheters", Chapter 6, Practical Angioplasty, Raven Press, New York, 1993 pp. 43–52.

"Selection of Balloon Catheters and Guidewires", Chapter 7, Practical Angioplasty, Raven Press, New York 1993.

*Primary Examiner*—Michael Buiz
*Assistant Examiner*—Kevin Truong
*Attorney, Agent, or Firm*—Morgan & Finnegan, L.L.P.

[57] ABSTRACT

Apparatus for suturing a wound in a body cannula having an axis extending between a proximal end and a distal end. A handle is disposed at the proximal end and a pair of needles disposed at the distal end, the needles being movable between a proximal position and a distal position. A suture manipulator carried by the cannula is insertable through the wound and operable to manipulate the suture into an engaging relationship with the needles on the far side of the body wall. A finger tab is movable on the handle in a single distal direction through multiple stage. In a first stage the needles are deployed; in a second stage, the suture manipulator is activated to thread the needles; and in a third stage the suture is released from a tensioning mechanism. In an associated method the needles are threaded on the far side of the body wall and withdrawn from the wound providing access to the suture ends on the near side of the body wall. Tying the suture ends closes the wound.

11 Claims, 6 Drawing Sheets

U.S. PATENT DOCUMENTS

| | | | |
|---|---|---|---|
| 5,417,699 | 5/1995 | Klein et al. | 606/144 |
| 5,458,609 | 10/1995 | Gordon et al. | |
| 5,462,561 | 10/1995 | Voda. | |
| 5,470,338 | 11/1995 | Whitfield et al. | |
| 5,474,568 | 12/1995 | Scott. | |
| 5,476,470 | 12/1995 | Fitzgibbons, Jr. | 606/144 |
| 5,496,332 | 3/1996 | Sierra et al. | |
| 5,573,540 | 11/1996 | Yoon. | |

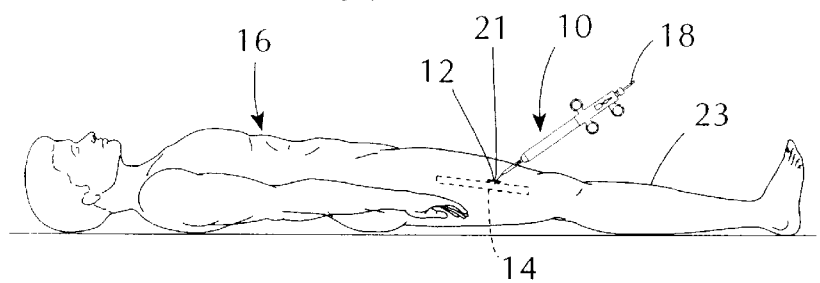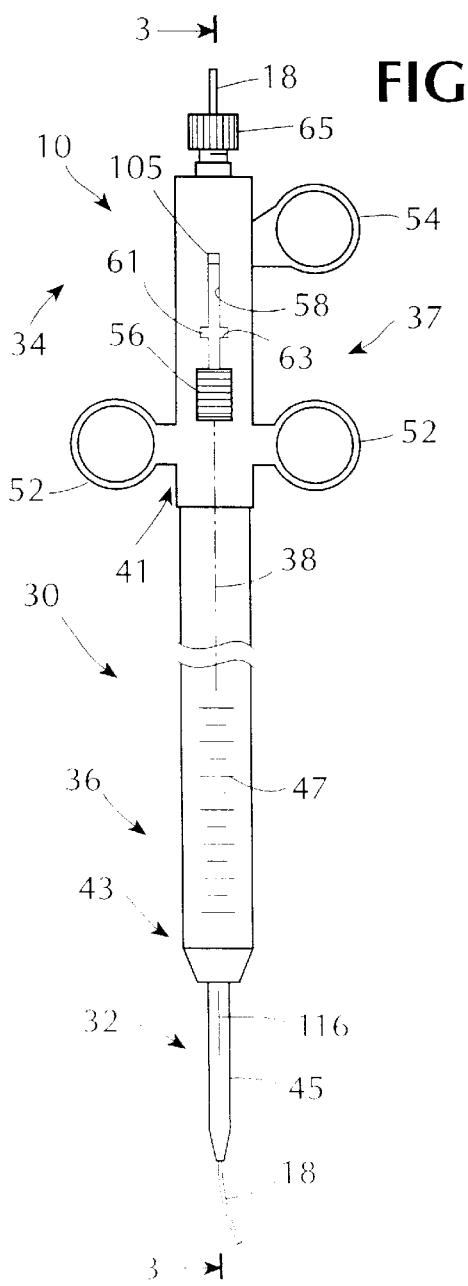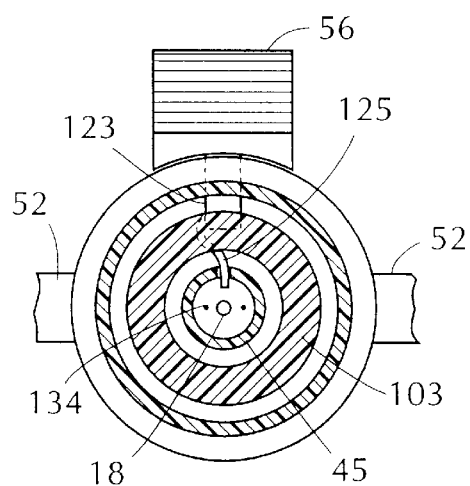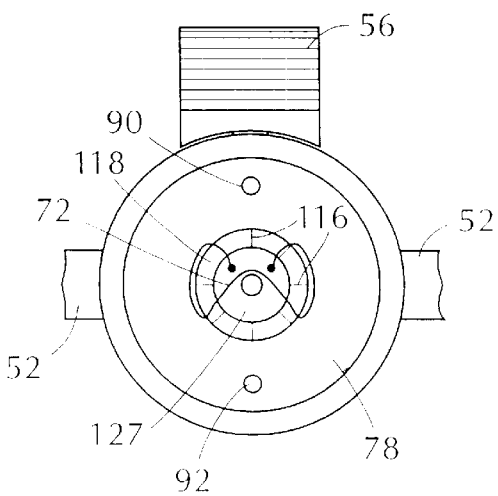

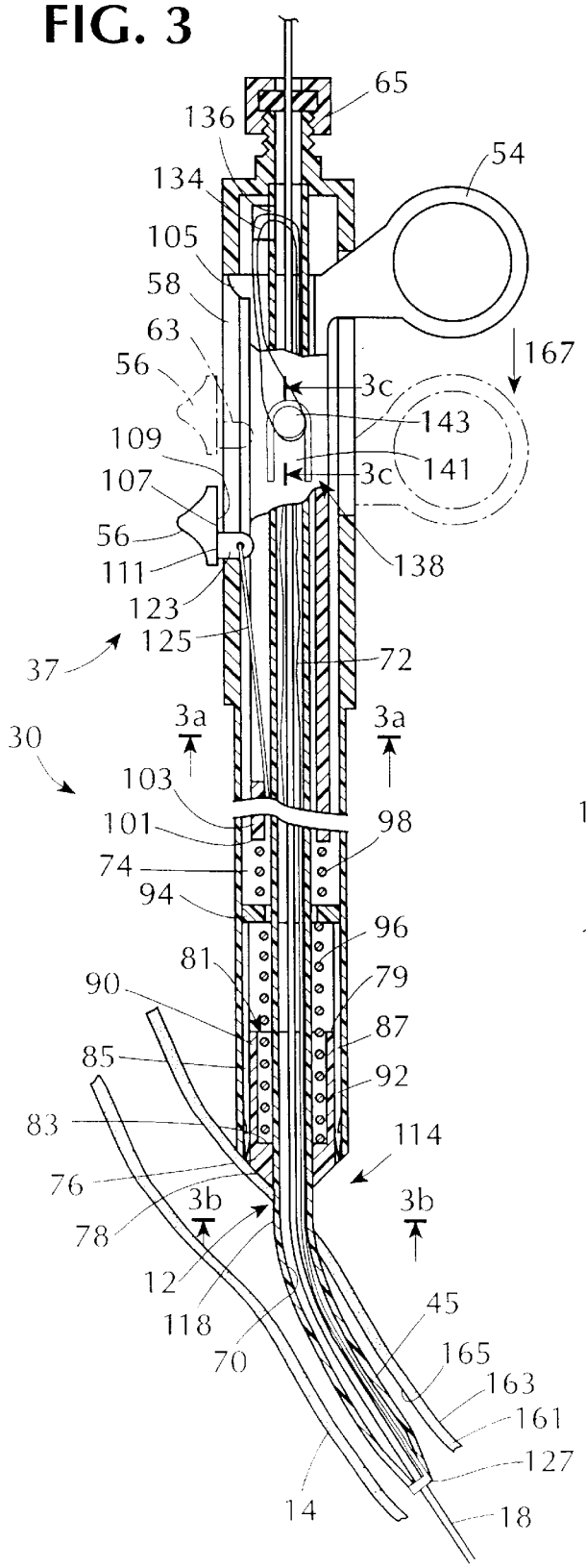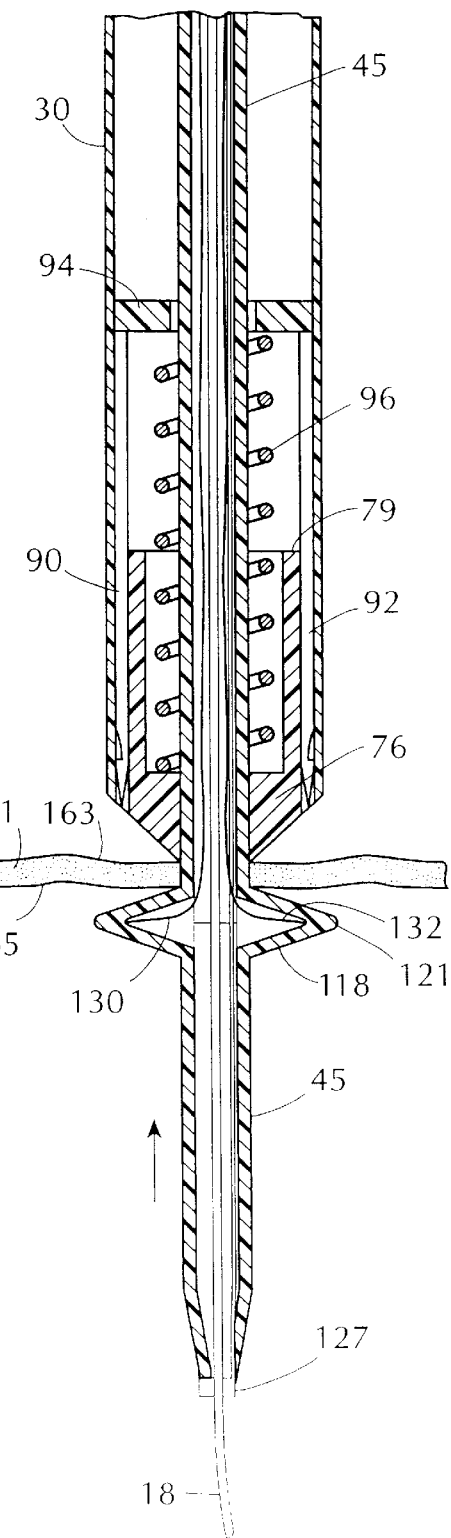

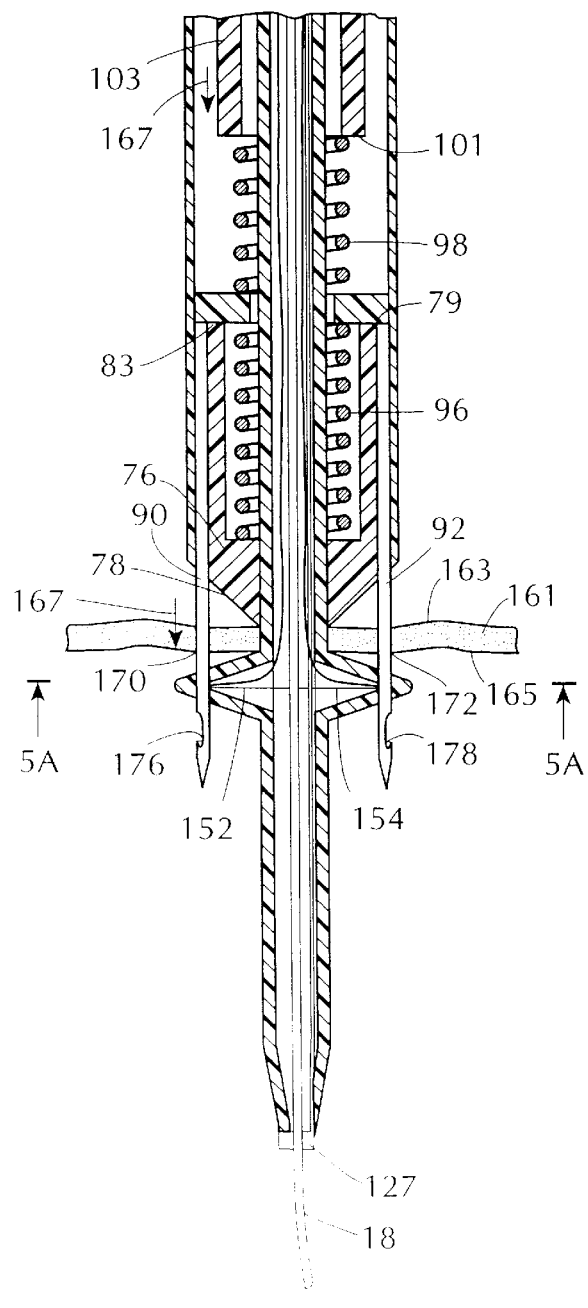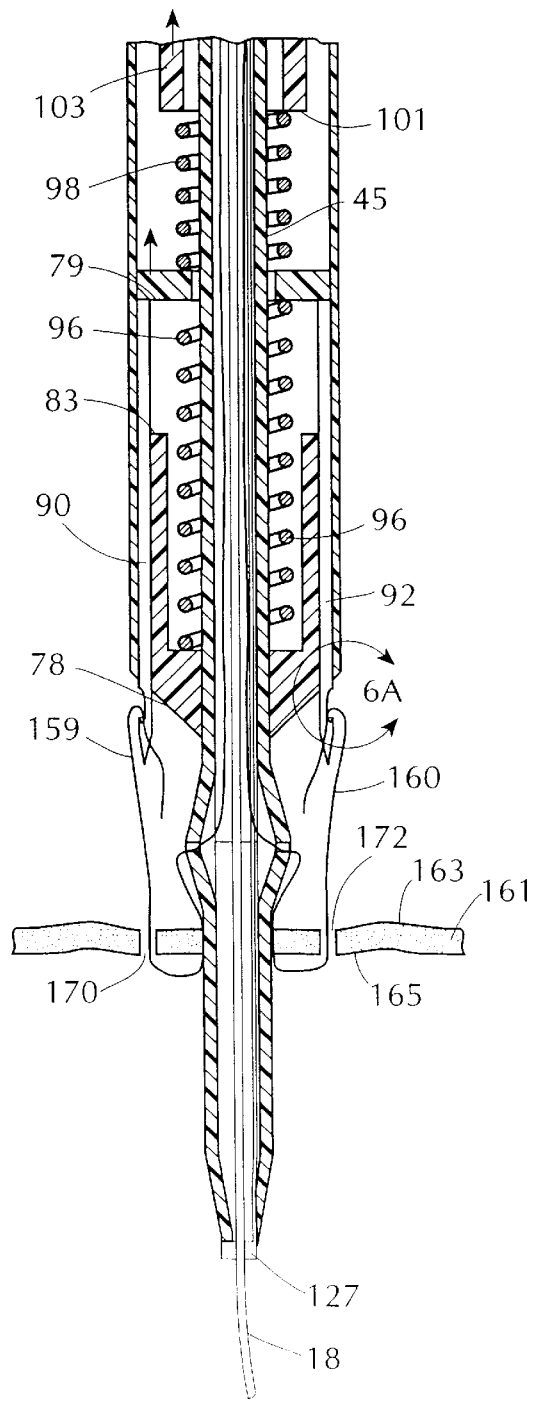

WOUND CLOSURE APPARATUS AND METHOD

This is a continuation of application Ser. No. 08/502,482 filed Jul. 14, 1995 now U.S. Pat. No. 5,700,273.

BACKGROUND OF THE INVENTION

1. Field of the Invention

This invention relates generally to apparatus and methods for closing a wound or hole in a body wall, and more specifically to wound closure devices using suture material.

2. Discussion of the Prior Art

A puncture-type wound in a body wall can be created either unintentionally, or intentionally as part of a surgical procedure. In either case, the wound typically has the configuration of a hole extending through the body wall where access to the far side of the wall is available only through the wound.

The wound in the body wall may be accidentally created but it is more likely that it will be intentionally created in a surgical procedure associated with interventional cardiology, for example.

Surgical procedures involving interventional cardiology commonly produce a wound in the femoral or iliac artery of the patient. In this case, the body wall in which the wound is formed is the wall of the artery which is disposed some distance beneath the skin of the patient. When these arteries are punctured, wounds or holes are left in the tissue wall forming the arteries. Currently, large caliber access sheaths and dilators are used which merely accentuate the size of the wound and demand an appropriate suturing apparatus and technique for closing the wound. Wounds of this type have been addressed with direct hand pressure or specialized weights, bandages and dressings. These implements, requiring placement for extended supervised periods of time, also result in considerable discomfort to the patient. Other types of closure devices include bioresorbable plugs which in some cases provide a matrix which facilitates clotting. More recently, devices have been used which include needles and attached sutures which have been inserted into the vessel. The needles have been driven outwardly through the wall of the vessel where the suture ends have been captured and retrieved for knot tying.

Similar devices are represented by U.S. Pat. No. 5,417,699 which disclose a pair of proximally facing needles insertable through the wound and radially expandable so that upon retraction of the device the needles extend through holes in the surrounding tissue. The prethreaded holes are then drawn outwardly through the tissue wall along with the ends of attached sutures. This construction requires a special needle capture mechanism to pull the needles proximally through the body wall.

SUMMARY OF THE INVENTION

The wound closure device of the present invention includes a distal cannula which is insertable through the wound and functions to provide a suture on the far side of the body wall. A handle of the device remains on the near side of the body wall. A finger tab operable on the handle manipulates the suture on the far side of the body wall between radially spaced outer and inner positions. A needle deployment mechanism, also operable on the handle, deploys needles from a proximal position to a distal position. In the distal position, the needles extend through needle holes in the surrounding tissue of the body wall, and into proximity with the suture on the far side of the body wall. In this position, the needles are disposed between the first and second positions of the suture so that manipulation of the suture between the first and second positions results in engaging the needle. The needles can then be withdrawn to capture the ends of the suture and to bring those ends through the needle holes to the near side of the body wall. At this point, the entire wound closure device can be retracted leaving the suture ends extending through tissue on opposite sides of the wound. Tying a knot between these ends tightens the suture across the wound to accomplish closure.

The apparatus for threading the needle on the far side of the body wall can include a Mallicot structure legs which is radially expandable and contractible to move the suture into threading engagement with the needles. This mechanism is operable from the handle of the apparatus on the near side of the body wall.

Apparatus for deploying the needles between the proximal and distal positions is also operable from the handle. This apparatus not only moves the needle but also trips the threading mechanism when the needles are appropriately positioned for threading. Further operation of the deployment mechanism frees the suture loop from a tensioning mechanism after the needles have been threaded, thereby permitting the apparatus to be withdrawn from the wound with the suture appropriately positioned to facilitate closure of the wound.

In one aspect of the invention, a wound closure apparatus is adapted for suturing a wound in a tissue wall. The apparatus includes a cannula having an axis extending between a proximal end and a distal end. A handle is disposed at the proximal end of the cannula. At least one pair of needles is disposed in proximity to the distal end of the cannula, the needle being movable between a proximal position and a distal position wherein the needle extends through the tissue wall. A suture manipulator carried by the cannula is insertable through the wound and operable to manipulate the suture into an engaging relationship with the needle when the needle is in the distal position.

An associated method results in suturing a wound formed in tissue of a body wall having a near side and a far side. Steps of the method include providing a suture having a first end, a second end, and a suture loop extending therebetween. The first and second ends of the suture are inserted through the wound leaving the suture loop on the near side of the body wall. Inserting an unthreaded first needle and an unthreaded second needle through the tissue places the distal ends of the needles on the far side of the body wall. The method also includes the steps of threading the first and second needles on the far side of the wall with respective ends of the suture, and withdrawing the threaded needles together with the associated first and second ends of the sutures to the near side of the body wall. Then the suture ends can be tensioned to draw the suture loop to the far side of the body wall, and tied to draw the tissue into proximity and thereby close the wound in the body wall.

DESCRIPTION OF THE DRAWINGS

FIG. 1 is a side elevation view of a patient and illustrating one embodiment of a wound closure apparatus of the present invention being used to close a wound in the femoral artery of the patient;

FIG. 2 is a front elevation view of one embodiment of the wound closure apparatus illustrated in FIG. 1;

FIG. 3 is an axial cross section view of the apparatus taken along lines 3—3 of FIG. 2;

FIG. 3A is a radial cross section view taken along lines 3A—3A of FIG. 3;

FIG. 3B is a radial cross section view taken along lines 3B—3B of FIG. 3;

FIG. 4 is an axial cross section view similar to FIG. 3 and showing one embodiment of a suture deployment mechanism associated with the present invention;

FIG. 5 is an axial cross section view similar to FIG. 4 and showing one embodiment of a needle deployment mechanism associated with the present invention, the needle mechanism being illustrated in a distal position suitable for threading the needles;

FIG. 6 is an axial cross section view similar to FIG. 5 and showing the needles in a retracted position after being threaded;

DESCRIPTION OF PREFERRED EMBODIMENTS AND BEST MODE OF THE INVENTION

Figure 9:
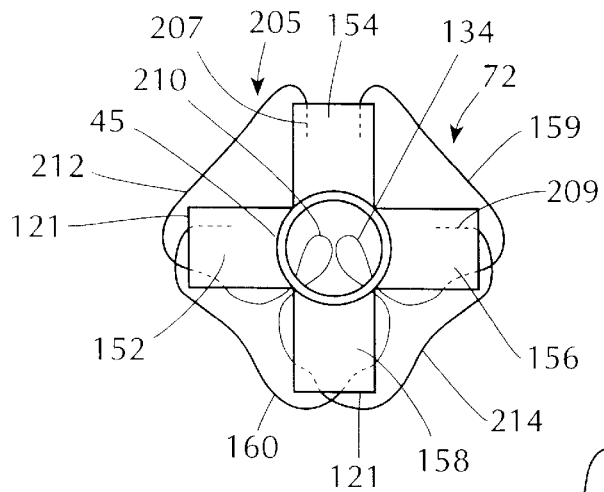
FIG. 9 is an end view similar to FIG. 5A and showing an alternate orientation of the suture to facilitate the threading of needles in an embodiment suitable for forming more than one pair of needle holes.

A wound closure apparatus is illustrated in FIG. 1 and designated generally by the reference numeral 10. The apparatus 10 is illustrated in use for closing a wound 12 in a femoral artery 14 of a patient 16. The wound 12 would typically have been intentionally created in order to provide access through the femoral artery 14 to the cardiovascular system of the patient 16. In this case, the wound 12 is formed in the tissue of a body wall which forms the femoral artery 14. Thus, portions of the femoral artery define the hole or wound 12 in the body wall. The apparatus 10 is typically introduced into the artery 14 over a guidewire 18 which extends through an incision 21 in the skin 23 of the patient 16.

It will be understood that although FIG. 1 illustrates the suturing of a wound 12 interiorly of the skin 23, the apparatus 10 is equally adapted for use in suturing a wound in any body wall including the skin 23.

A preferred embodiment of the wound closure apparatus 10 is illustrated in FIG. 2 and consists generally of a cannula 30 having a distal section 32, a proximal section 34, and an intermediate section 36. In this particular embodiment, the proximal section 34 comprises a handle 37, the distal section comprises a flexible catheter 45, and the intermediate section 36 comprises a generally rigid tube. The cannula 30 is otherwise defined by an axis 38 which extends between a proximal end 41 and a distal end 43 of the apparatus 10.

The cannula 30 is generally hollow in order to facilitate insertion of the apparatus 10 over the guidewire 18 which is shown at both the proximal and distal ends 41 and 43 respectively. Graduations 47 can be provided on the exterior surface of the intermediate section 36 in order to measure the depth of the wound 12 relative to the skin 23. Radiopaque marker rings can also be provided on the catheter 45 to facilitate fluoroscopic guidance and X-ray contrast.

The handle 37 includes a pair of stationary finger rings 52, and an actuator in the form of an axially movable finger ring 54 which is discussed in greater detail below. A finger tab 56 is also movable along the handle 37. This finger tab 56 rides within an elongate groove 58 which includes a slot 61 having a proximally facing shoulder 63. The embodiment of FIG. 2 is also provided with a Touhy-Borst valve 65 which can be tightened to seal against the guidewire 18. Back-bleeding through the catheter 45 can be evidenced through the Touhy-Borst valve 65 to provide a visual indication that the catheter 45 is located within the artery 14.

Figure 3C:
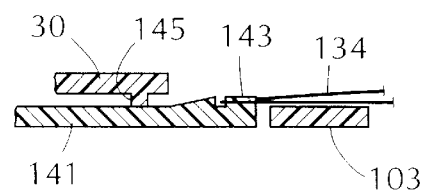
FIG. 3C is a cross-section view of a suture tensioning mechanism taken along lines 3C—3C of FIG. 3.

The interior regions of the cannula 30 are illustrated in FIG. 3. From this view it can be seen that the catheter 45 in this particular embodiment extends from the proximal end 41 and exits the cannula 30 through the distal end 43. Thus the catheter 45 forms a hollow tube within the hollow tube of the cannula 30. An inner channel 70 associated with the catheter 45 is adapted to receive not only the guidewire 18, but also a suture 72 which is described in greater detail below. An inner channel 74 associated with the cannula 30 is provided with a plug 76 at its distal end 43. This plug 76 has a distally facing outer surface 78, a proximally facing shoulder 79, and an annular recess 81 terminating within the channel 74 at a proximally facing surface 83. Radially outwardly of the recess 81, a pair of longitudinal needle bores 85, 87 are provided which extend generally parallel to the axis 38 from the cannula channel 74 to the outer surface 78.

A pair of needles 90, 92 are mounted for reciprocal movement within the respective bores 85 and 87. These needles 90, 92 are carried by a common radial flange 94 which is disposed within the channel 74 of the cannula 30 but is suitably apertured to receive the catheter 45 along the axis 38. On the distal side of the flange 94, a needle return spring 96 is disposed to extend from the surface 83 of the recess 81 to the flange 94. On the proximal side of the flange 94, a travel slack spring 98 extends from the flange 94 to a distally facing surface 101 of an elongate cylinder 103. This cylinder 103, which is disposed coaxial with and interiorly of the cannula 30, and is moveable by operation of the finger ring 54 within the channel 74 of the cannula 30. The catheter 45 extends through the cylinder 103 so that the cylinder 103 occupies a generally cylindrical space between the catheter 45 and the cannula 30.

In this embodiment of the wound closure apparatus 10, the finger ring 54 and attached cylinder 103 together with the springs 96, 98, the needles 90, 92 and associated flange 94 function as a deployment mechanism to initially deploy and ultimately retract the needles 90, 92. As the finger ring 54 is moved distally, the surface 101 of the cylinder 103 presses against the spring 98 which in turn forces the flange 94 and attached needles 90, 92 distally against the bias of the spring 96. Thus, distal pressure on of the finger ring 54 moves the needles 90, 92 from a proximal position best illustrated in FIG. 3 to a distal position best illustrated in FIG. 5.

Figure 5A:
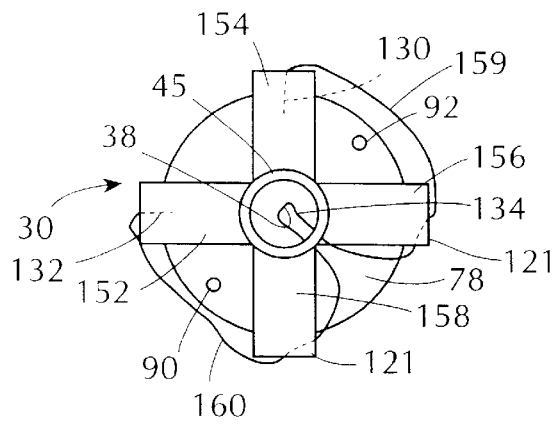
FIG. 5A is a radial cross-section view taken along lines 5A—5A of FIG. 5, and showing the suture deployment mechanism in an expanded state prior to threading.
Figure 5B:
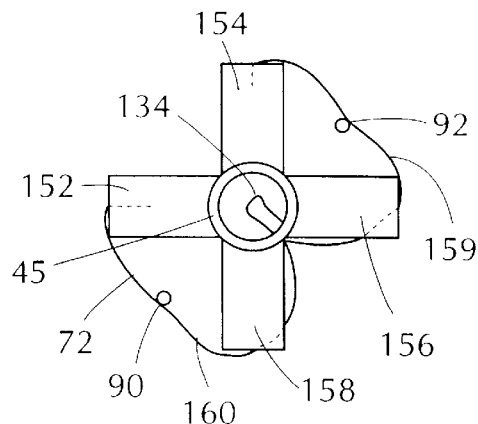
FIG. 5B is a radial cross-section view similar to FIG. 5A and showing the suture deployment mechanism in a radially contracted state with the suture tightly held against the needles for threading.

When the finger ring 54 is moved backwardly or proximally, the cylinder 103 withdraws from the spring 98 and the force of the compressed spring on the flange 94 causes the needles 90, 92 to return from the distal position illustrated in FIG. 5 toward the proximal position illustrated in FIG. 3. The combination of the cylinder 103 and finger ring 54 is also provided with a trip mechanism in the form of a tang 105 which rides within the groove 58 to engage a flange 107 on the finger tab 56. This flange 107 has an inclined surface 109 and a distal facing shoulder 111, discussed in greater detail below.

A suture deployment mechanism 114 can be formed as part of the catheter 45 in general proximity to the distal surface 78 associated with the cannula 30.

Figure 6A:
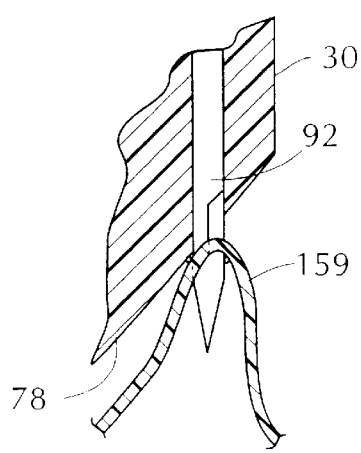
FIG. 6A is an enlarged view of the threaded needles in the retracted position illustrated in FIG. 6.

In a preferred embodiment, this suture manipulating mechanism 114 is formed by a plurality of slits 116 (best shown in the radial cross section view of FIG. 3B) which are spaced around the circumference of the catheter 45. These slits 116 define a plurality of fingers 118 perhaps best shown in FIG. 5A. Each of the fingers 118 can be provided with an intermediated living hinge 121 which facilitates radial expansion of the fingers 118 when the catheter 45 is axially compressed. This radial expansion occurs between a first position illustrated in FIG. 3, where the fingers 118 have a relatively low profile, to a second position illustrated in FIG. 4, where the fingers 118 have a relatively high radial profile. In combination, the expandable fingers 118 form a device commonly referred to as a Mallicot structure. Between the first, low profile position and the second, high profile position of the fingers 118, there exists a natural position described below with reference to FIG. 6.

The suture manipulating mechanism 114 also includes the finger tab 56 and a projection 123 which extends from the tab 56 through the groove 58 and into the channel 74 of the cannula 30. An elongate element 125 is fixed at its proximal end to the a projection 123 and at its distal end to a flange 127 at the distal tip of the apparatus 10. This flange 127, which is apertured to receive the guidewire 18, is at least as large as the catheter 45 at the distal end 43 of the apparatus 10. It is the purpose of the finger tab 56, the element 125 and the flange 127 to move the fingers 118 between the low profile position and the high profile position. As the finger tab 56 is moved proximally, from the solid line position to the dotted line position in FIG. 3, the element 125 is tensioned thereby drawing the distal flange 127 proximally. This creates an axial compression force on the catheter 45 which causes each of the fingers 118 to buckle at its ends and at the associated living hinge 21 thereby resulting in expansion of the finger 118 forming the Mallicot structure.

These fingers 118 can be maintained in the second, expanded position automatically by ensuring that the flange 107 associated with the finger tab 56 is appropriately lodged within the slot 61 associated with the groove 58. Thus, the finger tab 56 can be locked in the proximal, dotted position when the flange 107 falls into the slot 61 and the distally facing surface 111 of the flange 107 engages the proximally facing surface 63 of the slot 61. The resulting lock, which holds the tab 56 in its proximal position and holds the fingers 118 in their second expanded state, is released in a preferred embodiment when the tab 105 associated with the finger ring 54 and cylinder 103 engages the flange 107 forcing it out of the slot 61. When the lock is released, it is the natural tendency of the fingers 118 to move back toward the low profile state. This forces the distal flange 127 distally tensioning the element 125 and drawing the finger tab 56 distally, from the dotted position to the solid line position in FIG. 3. Distal finger pressure on the tab 56 can also facilitate movement of the fingers 118 from the high profile state toward the low profile state if the elongate element 125 can accommodate a compressive load.

This operation of the suture manipulating mechanism 114 and the expandable fingers 118 make this structure particularly useful in deploying the suture 72. As best illustrated in FIGS. 3 and 4, the suture 72 includes free ends 130 and 132 which can be embedded in or near the living hinge 121 of adjacent fingers 118. Between the ends 130 and 132, the suture forms a suture loop 134 which is relatively long and extends from the fingers 118 into the channel 70 of the catheter 45 and along substantially the entire length of the cannula 30 where it exits the catheter 45 through a pathway or hole 136.

Exteriorly of the catheter 45, the suture loop 134 engages a suture tensioning device 138 in the form of a tab 141 formed in the wall of the cylinder 103. This tab 141 includes a post 143 which extends radially outwardly to receive the suture loop 134. The tab 141 is compressible radially inwardly by a projection 145 on the inner surface of the handle 37. As the cylinder 103 moves axially, by operation of the finger ring 54, the projection 145 engages the tab 141 and moves it radially inwardly. This causes the suture 72 to clear the post 143 effectively dislodging the suture loop 134 from the tensioning device 138. This feature is particularly advantageous during operation of the apparatus 10 for reasons discussed in greater detail below.

A preferred method for attaching the suture 72 to the fingers 118 can be best understood with reference to FIG. 5A. In this embodiment, the fingers 118 are further designated by the reference numerals 152, 154, 156, and 158. In the view of FIG. 5A, the fingers 152–158 are fully extended in the second position. The associated living hinges 121 are disposed at the bends of the fingers 152–158 where the fingers reach their maximum radial distance from the axis 38.

With such an embodiment, the suture end 130 can be loosely embedded in the finger 154, the suture can then be led from the finger 154 and through a slit in the living hinge 121 associated with the finger 156. From this point, the suture loop 134 can be fed into the catheter 45 and along the length of the cannula 30. In a similar manner, the suture end 132 can be loosely embedded in the finger 152 and led through a slit in the living hinge 121 associated with the leg 158. With this orientation, each of the suture ends 130, 132 forms a short section of suture which extends between adjacent legs. Thus, the suture end 130 extends between adjacent legs 154, 156 to form a suture portion 159, while the suture end 132 extends between opposing adjacent legs 152, 158 to form a suture portion 160.

Loading of the wound closure apparatus 10 can be accomplished during the final stage of manufacture. The finger tab 56 on the handle 37 is initially set to the distal position illustrated by the solid lines in FIG. 3. This ensures that the fingers 118 forming the Mallicot structure are in the low profile state. The suture 72 can then be mounted on the fingers 118 and the suture loop 134 and threaded through the channel 70 of the catheter 45. After exiting the hole 136 in the catheter 45, the suture loop 134 is disposed around the post 143 in the suture tensioner 138. Finally, the movable finger ring 54 is placed in its proximal position so that the needles 90, 92 are retracted into the associated bores 85, 87. The Touhy-Borst valve 65 can also be to loosened to allow insertion over the guidewire 18.

Operation of the wound closure apparatus is begun by inserting the catheter 45 into the wound 12. If the wound 12 is in the skin 23 of the patient 16, the catheter 45 is introduced directly into the wound 12. If however, as illustrated in FIG. 1, the wound occurs in a body wall, such as the wall of the femoral artery 14, the small incision 21 can be made in the skin 23 in order to gain access to the artery 14. The guidewire 18 will typically have been placed through the incision 21 and wound 12 as part of the surgical procedure which developed the wound 12.

With the guidewire 18 in place, the apparatus 10 can be positioned over the guidewire 18 so that the distal tip of the catheter 45 follows the guidewire through the incision 21 and the wound 12 into the artery 14. At this point, the graduations 47 on the cannula 30 will provide an indication of the depth of the artery 14 relative to the skin 23. Radiopaque markers on the catheter 45 can be useful to facilitate fluoroscopic guidance to an operative position. The Touhy-Borst valve 65 also provides a visual indication of backbleeding which would evidence proper placement within a blood vessel. The valve 65 can also be provided with a T-fitting to facilitate injections of X-ray contrast media through the catheter 45.

With reference to FIG. 3, it will be noted that the body wall, in this case a body wall 161 of the artery 14, has a near side 163 and a far side 165. Since access to the far side 165 of the body wall 161 is severely limited, it is of particular advantage to the present invention that wound closure can be achieved without direct access to the far side 165 except through the wound 12.

In the preferred method, the catheter 45 is inserted through the wound 12 a distance sufficient that the fingers 118 forming a Mallicot structure are positioned on the far side 165 of the body wall 161. The cannula 30 including the needles 90 and 92, remain on the near side 163 of the body wall 161. With this orientation, it will be noted that the suture ends 130, 132 illustrated in FIG. 4 are positioned on the far side 165 while the suture loop 134 is positioned on the near side 163 of the body wall 161.

This preferred operative position for the apparatus 10 is achieved by operation of the handle 37 and associated stationary rings 52. With the apparatus 10 thus disposed, the fingers can be expanded from their first low profile state illustrated in FIG. 3 to their second expanded state illustrated in FIG. 4. Note that this expansion of the fingers 118 results in the radial outward movement of the suture portion 159, 160.

With the suture portions 159, 160 appropriately positioned, the needles 90, 92 can now be deployed. These needles 90, 92 are initially disposed in their associated bores 85, 87 on the near side 163 of the body wall 161. Deployment of the needles 90, 92 is accomplished by moving the finger ring 54 and associated cylinder 103 distally in the direction of an arrow 167 in FIG. 5. The distally facing surface 101 of the cylinder 103 compresses the spring 98 which in turn exerts a force on the needle flange 94. This force, which is increased with further distal movement of the finger ring 54 against the bias of the spring 96, moves the needles 90, 92 beyond the distal surface 78 and through needle holes 170 and 172 respectively, in the body wall 161. Distal movement of the needles 90, 92 ceases when the flange 94 bottoms out on the proximal facing surface 79 of the plug 76.

The needles 90, 92 each have a needle eye 176, 178 respectively, which in a preferred embodiment is in the form of a French eye. When the needles 90, 92 are fully extended, these eyes 176, 178 are preferably disposed on the far side 165 of the body wall 161 and beyond the suture portions 152, 154. With the suture portions 159, 160 in their radially extended position, the needles 90, 92 in their distal-most position, and the needle eyes 176, 178 facing the suture portions 152, 154, the suture 72 can now be manipulated to thread the needles 90, 92.

In a preferred embodiment, this manipulation of the suture 72 is accomplished by further distal movement of the finger ring 54 to a second position where the tang 105, riding within the groove 58, engages the inclined surface 109 of the flange 107. This engagement of the flange 107 by the tang 105 releases the finger tab 56 from its locked proximal position. This relieves tension on the element 125 and enables the fingers 118 to radially compress naturally as the catheter 45 elongates. The radial compression of the fingers 118 moves the suture portions 159, 160 against the associated needles 90, 92 at a position proximal to the eyes 176, 178.

Of course with the radial compression of the fingers 118, the distance between the adjacent living hinges 121 is reduced. This would normally cause the suture portions 152, 154 to become slack were it not for the suture tensioning mechanism 138 previously discussed. It will be noted that as the finger ring 54 is moved distally, the suture tensioning mechanism also moves distally. Since the hole 136 in the catheter 45 is disposed proximally of the tensioning mechanism 138, the distal movement of the mechanism 138 creates proximal movement of the suture loop through the catheter channel 70. This in turn tensions the suture portions 152 and 154 even as the fingers 118 are radially contracting.

To this point, distal movement of the finger ring 54 has operated to deploy the needles 90, 92 in a first position, and to manipulate the fingers 118 in order to thread the needles in a second position of the finger ring 54. This manipulation of the fingers 118 in the second position is accomplished while tensioning the sutures 72 with the mechanism 138.

Figure 3D:
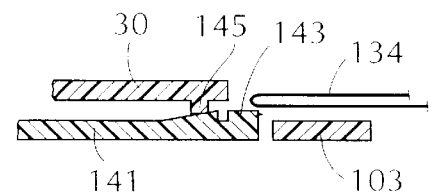
FIG. 3D is a cross-section view of the suture tensioning mechanism illustrated in FIG. 3C, the mechanism being deactivated to release the suture.

Further distal movement of the finger ring 54 to a third position results in removal of the suture loop 134 from the post 143 of the tensioner 138. This has the effect of releasing the suture loop 134 from the apparatus 10 so that it is free to be drawn into the wound 12. This freeing of the suture loop 134 is accomplished as illustrated in FIG. 3B when distal movement of the cylinder 103 brings the tab 141 into proximity with the projection 145 on the handle 37. This interfering relationship causes the tab 141 to compress radially inwardly thus forcing the suture loop 134 from the post 143 as illustrated in FIG. 3D.

It will be noted at this point that movement of the finger ring 54 in a common distal direction operates to perform three sequential steps in a method for operating the apparatus 10. In a first step associated with first distal position of the ring 54, the needles 90, 92 are deployed to a position where they can be threaded. In a second step associated with a second position of the ring 54, the finger tab 56 is released thereby permitting contraction of the fingers 118 to facilitate threading the needles 90, 92. In a third step associated with a third position of the finger ring 54, the suture loop 134 is released from the tensioning mechanism 138 to facilitate withdrawal of the apparatus 10.

With the suture portions 152, 154 tensioned radially against the needles 90, 92 proximally of the eyes 176, 178, the needles 90,92 can now be retracted. Initially this retraction of the needles 90, 92 causes the tensioned suture portions 159, 160 to enter the eyes 176, 178. Further retraction of the needles 90, 92 withdraws the captured suture portions 159, 160 through the associated needle holes 170, 172 in the skin 23. At this point, both of the suture ends 130, 132, as well as the suture loop 134, are disposed on the near side 163 of the wall 161. The apparatus 10 can now be withdrawn from the wound 12.

The needles 90, 92 are preferably retracted until the eyes 176, 178 enlarged by the presence of the suture portions 152, 154 are biased against the distal surface 78 at the distal end of the cannula 30. In this position of the needles 90, 92, illustrated in the enlarged view of FIG. 6A, the suture ends 130, 132 are trapped between the respective needles 90, 92 and the cannula 30 due to return spring force.

Figure 7:
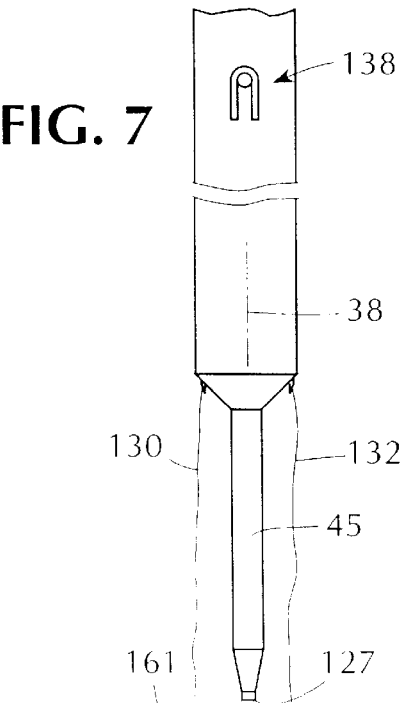
FIG. 7 is a side elevation view illustrating the wound closure apparatus fully removed from the wound with the suture ends extending through the surrounding body wall.

With the suture loop 134 released from the post 143 of the tensioner 138, removal of the apparatus 10 will draw the suture portions 159, 160 further away from the body wall 161 as illustrated in FIG. 7. This causes the suture loop 134 to be drawn distally through the catheter 45 until it exits from between adjacent legs 156, 158 and is drawn through the wound 12 to the far side 165 of the body wall 161.

Figure 8:
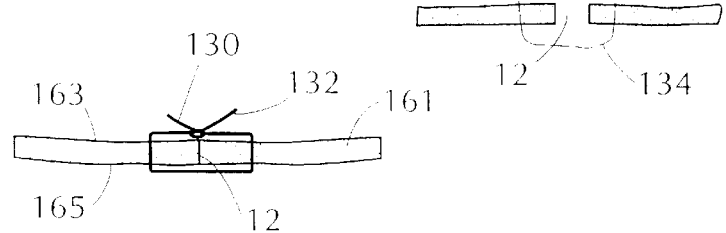
FIG. 8 is a side elevation view of the suture ends tied to close the wound in the body wall.

Once the wound closure apparatus 10 has been fully removed from the wound 12, the suture ends 130, 132 can be removed or cut from the fingers 118 and tied with a surgeon's knot in a conventional manner. Such a knot can be pushed through the incision 21 and into proximity with the wound 12 as illustrated in FIG. 8.

Figure 10:
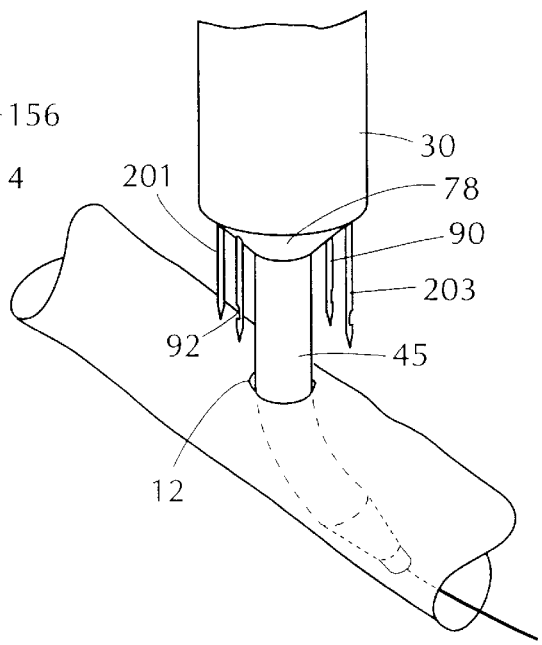
FIG. 10 is an elevation view of a further embodiment of the apparatus including two pairs of needles.
Figure 11:
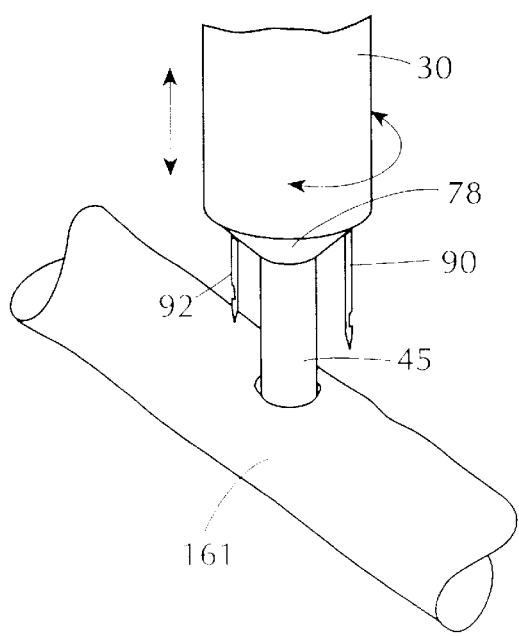
FIG. 11 is an elevation view of the wound closure apparatus being rotated so that a single pair of needles creates more than one pair of needle holes.

An additional embodiment of the invention is illustrated in FIG. 10 and includes two needle pairs. The needles 90 and 92 previously discussed form one of the needle pairs while an additional needle pair comprises needles 201 and 203. In this case, the four needles 90, 92, 201 and 203 are displaced 90° from each other around the distal surface 78 of the cannula 30. The needle deployment (not shown in FIG. 10) can be similar to that previously discussed where the four needles 90, 92, 201 and 203 are fixed to the common flange 94 (best illustrated in FIG. 4).

This embodiment of the invention functions to simultaneously apply two sutures to the wound 12. The first suture can be that previously referenced with the numeral 72. This suture can be laced to the suture manipulating mechanism illustrated in FIG. 9 in the same manner as discussed with reference to FIG. 5. A second color-coded suture 205 can also be laced on to the legs 152–158 of the Mallicot structure in the manner illustrated in FIG. 9.

This suture 205 having a first end 207 and a second end 209 is also characterized by a suture loop portion 210. In a preferred method, the end 207 of the suture 205 is loosely held in the leg 154 of the Mallicot structure. The suture is then laced through the living hinge 121 and the leg 152 with the suture loop 210 extending into the channel associated with the catheter 45. As the suture loop exits this channel, it can be passed through the living hinge 121 associated with the leg 158. Finally, the end 209 of the second suture 205 can be loosely embedded in the leg 156.

This configuration for the second suture 205 produces a suture portion 212 between the legs 152 and 154 and a second suture portion 214 between the legs 156 and 158. In this manner, the two sutures 72 and 205 can form the four suture portions 159, 160, 212 and 214 for the respective needles 90, 92, 201 and 203. The resulting suture deployment mechanism can be operated in the manner previously discussed to thread each of the four needles associated with the embodiment of FIG. 10.

The dual suture embodiment of the suture deployment mechanism illustrated in FIG. 9, can also be used with the two needle embodiment of the apparatus 10 previously discussed. In a preferred method of operation, the two needles 90–92 can be operated in the manner previously discussed to capture the suture portions 159 and 160. Then the cannula 30 and needles 90, 92 can be rotated 90° to function with respect to the suture portions 212 and 214. Of course in this embodiment, means must be provided for rotating the cannula 30, and needles 90, 92 relative to the legs 152–158 forming the Mallicot structure.

Figure 12:
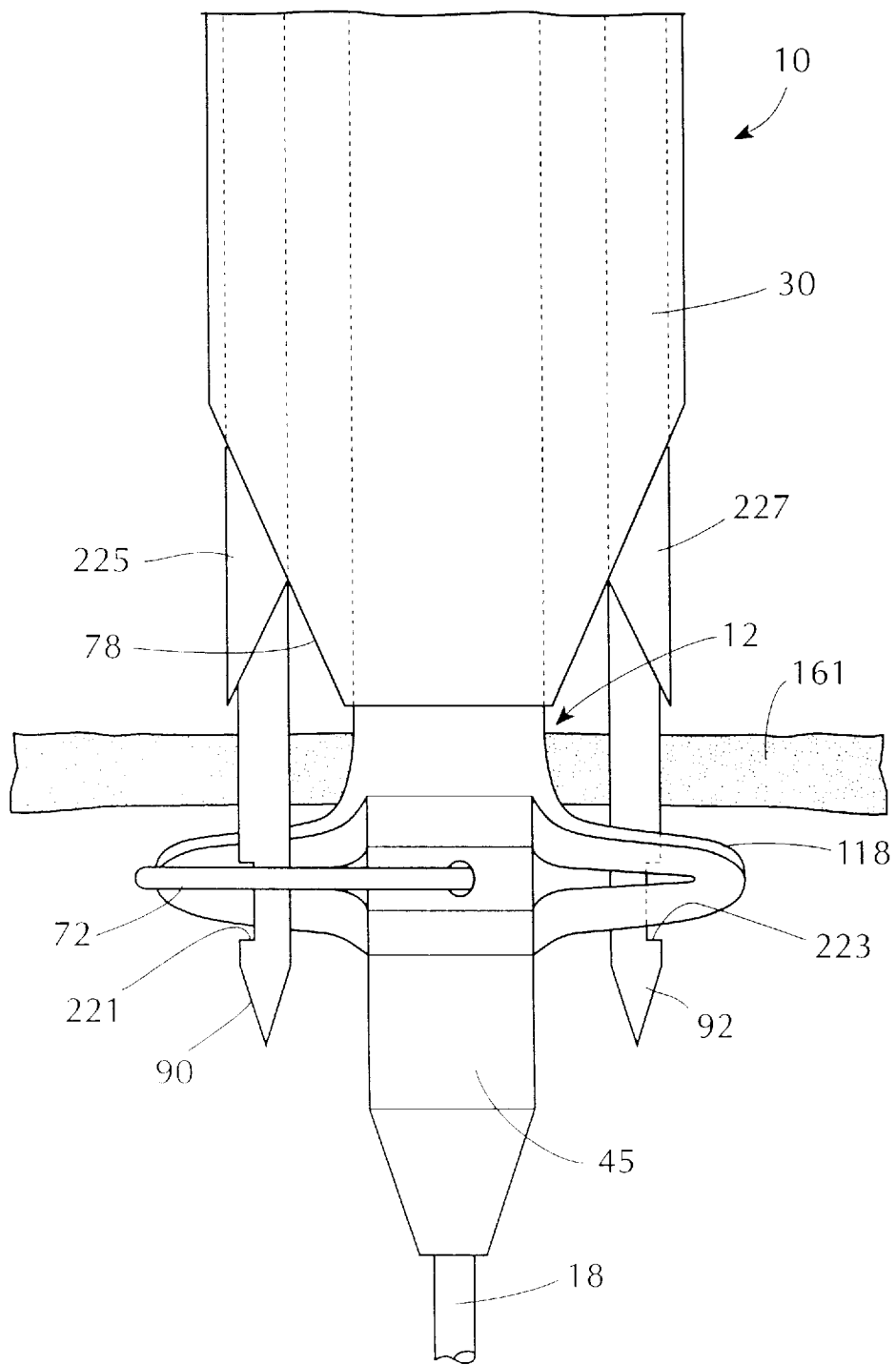
FIG. 12 is a side elevation view of a further embodiment of a wound closure apparatus including a pair of suture capture needles.

FIG. 12 illustrates a further embodiment of the wound closure apparatus 10. This embodiment includes the cannula 30 and catheter 45, as well as the fingers 118 and associated suture 72. The illustrated embodiment also includes the needles 90, 92, but in this case, the needle eyes (previously designated by the reference numerals 176, 178) are not formed as French eyes, but rather as mere slots 221, 223. As compared to the French eyes previously discussed, the slots 221, 223 can be formed with a significantly lesser depth. As a result, the needles 90, 92 can provided with a much smaller diameter.

The embodiment of FIG. 12 provides for effective suture capture with the provision of suture capture needles 225 and 227. These needles 225 and 227 can be provided with a tubular configuration and a telescoping relationship with the associated needles 90, 92. The distal ends of the suture capture needles 225, 227 can be sharpened to facilitate their deployment through the body wall 17.

Operation of the FIG. 12 embodiment proceeds in the manner previously discussed with the needles 90, 92 being deployed through the body wall 17. With the more narrow configuration of the needles 90, 92, this step of deploying the needles should be more easily accomplished than in the FIG. 5 embodiment. As the suture 72 is manipulated by the fingers 118 in the manner previously discussed, the suture 72 is drawn into the slots 221, 223 of the respective needles 90, 92. At this point, the suture capture needles 225, 227 can be deployed by moving them distally along the associated needles 90, 92. As the distal end of the capture needles 225, 227 approach the slots 221, 223, the suture 72 is pinched between the associated needles 90, 225 and 92, 227.

With the suture 72 appropriately captured in the slots 221, 223, the needles 90, 92 and associated capture needles 225, 227 can be withdrawn toward the cannula 30. Preferably after the needles 90, 92 and 225, 227 have cleared the body wall 17, the entire apparatus 10 can be withdrawn from the wound 12 as the method of closure continues in the manner previously described.

Given the wide variations in the concept embodied in the foregoing apparatus and methods, one is cautioned not to restrict the invention to the embodiments which have been specifically disclosed and illustrated, but rather is encouraged to determine the scope of the invention only with reference to the following claims.

We claim:

1. A method for suturing a wound in a body wall having a near side and a far side, comprising the steps of:

providing a wound closure apparatus including a proximal section, a distal section and an intermediate section;

inserting the distal section through the wound from the near side to the far side of the body wall;

deploying a pair of needles through the body wall surrounding the wound to form an associated pair of needle holes;

inserting a suture having two ends and a suture loop extending therebetween directly into and through the wound from the near side to the far side of the body wall;

manipulating the suture into threading engagement with the needles;

withdrawing the threaded needles through the needle holes to access the ends of the suture on the near side of the body wall; and withdrawing the distal section of the apparatus through the wound.

2. The method recited in claim 1, wherein the manipulating step includes the steps of moving the suture to engage the needle on the far side of the wall to thread the needle.

3. The method recited in claim 1 further comprising the step of:

tying the ends of the suture to each other to close the wound in the body wall.

4. The method recited in claim 1 wherein the providing step includes the step of:

providing the intermediate section in the form of a rigid tube having a proximal end and a distal end; and providing the distal section in the form of a flexible tube attached to the distal end of the rigid tube.

5. The method recited in claim 1 wherein the deploying step includes the steps of:

providing a deployment mechanism in the proximal section of the apparatus; and operating the deployment mechanism on the near side of the body wall to deploy the needles through the body wall.

6. A method for suturing a wound formed in tissue of a body wall having a near side and a far side, the method comprising the steps of:

providing a suture having a first and a second end, and a suture loop extending therebetween;

inserting an unthreaded first needle and an unthreaded second needle through the tissue;

inserting the first end and the second end of the suture directly into and through the wound leaving the suture loop on the near side of the body wall;

manipulating the suture into threading engagement with the needles;

withdrawing the threaded needles and the associated first and second end of the suture through the tissue;

tensioning at least one of a first and second ends of the suture on the near side of the wall to draw the suture loop to the far side of the body wall; and tying the first end to the second end of the suture to close the wound formed in the tissue of the body wall.

7. The method recited in claim 6 wherein the needles are threaded substantially simultaneously.

8. The method recited in claim 6 further comprising the steps of:

during the tensioning steps, engaging the suture loop on the near side of the body wall to tension the first and second ends of the suture on the far side of the body wall; and during the withdrawing step, disengaging the suture loop on the near side of the body wall to draw the suture loop to the far side of the body wall.

9. A wound closure apparatus for suturing a wound in a tissue wall, comprising:

a cannula having an axis extending between a proximal end and a distal end;

a handle disposed at the proximal end of the cannula;

at least one needle disposed in proximity to the distal end of the cannula, the needle being movable between a proximal position and a distal position adjacent to the wound to be closed; and a suture manipulator carried by the cannula and being insertable directly into and through the wound, the manipulator being operable to manipulate the suture into threading engagement with the needle when the needle is in the distal position.

10. The wound closure apparatus recited in claim 9 further comprising:

a finger tab disposed on the handle and coupled to the suture manipulator, the tab being movable relative to the handle to operate the manipulator so that the suture moves between a first position and a second position disposed radially outwardly of the first position.

11. The wound closure apparatus recited in claim 10 wherein:

the needle in the distal position is positioned generally parallel to the axis of the cannula and is disposed generally a first distance from the axis of the cannula;

the suture in the first position is positioned generally parallel to the axis of the cannula and is disposed generally a second distance from the axis of the cannula, the second distance being less than the first distance; and the suture in the second position is positioned generally parallel to the axis of the cannula and is disposed generally a third distance from the axis of the cannula, the third distance being greater than the second distance.

* * * * *